(12) United States Patent
Nilsson et al.

(10) Patent No.: US 6,756,377 B2
(45) Date of Patent: *Jun. 29, 2004

(54) COMPOUNDS AND THEIR USE

(75) Inventors: Björn M. Nilsson, Uppsala (SE); Martin Scobie, Uppsala (SE)

(73) Assignee: Biovitrum AB, Stockholm (SE)

(*) Notice: Subject to any disclaimer, the term of this patent is extended or adjusted under 35 U.S.C. 154(b) by 0 days.

This patent is subject to a terminal disclaimer.

(21) Appl. No.: 09/988,966

(22) Filed: Nov. 19, 2001

(65) Prior Publication Data
US 2002/0103204 A1 Aug. 1, 2002

Related U.S. Application Data
(60) Provisional application No. 60/253,702, filed on Nov. 28, 2000.

(30) Foreign Application Priority Data
Nov. 20, 2000 (SE) ................................. 0004244

(51) Int. Cl.[7] ..................... A61K 31/497; C07D 401/04

(52) U.S. Cl. ........................ 514/252.11; 514/235.8; 544/120; 544/357

(58) Field of Search ............................. 544/120, 357; 514/252.11, 235.8

(56) References Cited

U.S. PATENT DOCUMENTS
4,081,542 A 3/1978 Lumma, Jr. et al. ........ 424/250
6,465,467 B1 * 10/2002 Nilsson et al.

FOREIGN PATENT DOCUMENTS
| JP | 11-279159 | 10/1999 | .......... C07D/241/04 |
| WO | WO 96/11930 | 4/1996 | .......... C07D/471/04 |
| WO | WO 00/76984 | 12/2000 | .......... C07D/241/18 |

OTHER PUBLICATIONS

Gaster et al in "Annual Reports in Medicinal Chemistry", vol. 33. pp. 21–30 (1998).*
K.-E. Andersson, "Pharmacology of Penile Erection", *Pharmacological Reviews*, vol. 53, No. 3, pp. 417–450 (2001).
Anibal A. Arjona et al., "Effect of a 5–HT$_{2c}$ serotonin agonist, dexnorfenfluramine, on amyloid precursor protein metabolism in guinea pigs", *Brain Research*, 951, pp. 135–140 (2002).
M. Bancila et al., "5–Hydroxytryptamine$_{2c}$ Receptors on Spinal Neurons Controlling Penile Erection in the Rat", *Neuroscience*, vol. 92, No. 4, pp. 1523–1537 (1999).
Mike J. Bickerdike et al., "5–HT$_{2c}$ receptor modulation and the treatment of obesity", *Diabetes, Obesity and Metabolism*, pp. 207–214 (1999).
Ewa Chojnacka–Wójcik et al., "Involvement of 5–HT$_{2c}$ Receptors in the m–CPP–Induced Antinociception in Mice", *Pol. J. Pharmacol.*, vol. 46, pp. 423–428 (1994).

Florence Clenet et al., "Involvement of 5–HT$_{2c}$ receptors in the anti–immobility effects of antidepressants in the forced swimming test in mice", *European Neuropsychopharmacology*, vol. 11, pp. 145–152 (2001).
John F. Cryan et al., "Antidepressant–Like Behavioral Effects Mediated by 5–Hydroxytryptamine$_{2c}$ Receptors[1]" *The Journal of Pharmacology and Experimental Therapeutics*, vol. 295, No. 3, pp. 1120–1126 (2000).
S.N. Eǧe, "The Chemistry of hererocyclic Compounds" *Organic Chemistry*, pp 1009–1011 (1984).
Lawrence W. Fitzgerald et al., "Chapter 3: 5–HT$_{2c}$ Receptor Modulators: Progress in Development of New CNS Medicines", *Annual Reports in Medicinal Chemistry*, vol. 37, pp. 21–30 (2002).
Laramie M. Gaster et al., "Chapter 3. Latest Developments in Serotonin Receptor Modulation", *Annual Reports in Medicinal Chemistry*, vol. 33, pp. 21–30 (1998).
Goodman and Gilman's, "Biotransformation of Drugs" *The Pharmacological Basis of Therapeutics*, 8th ed., McGraw–Hill, Int. Ed. 1992, p. 13–18.
A.J. Grottick et al., "Activation of 5–HT$_{2c}$ receptors reduces the locomotor and rewarding effects of nicotine", *Psychopharmacology*, vol. 157, pp. 292–298 (2001).
Andrew J. Grottick et al., "Studies to Investigate the Role of 5–HT$_{2c}$ Receptors on Cocaine–and Food–Maintained Behavior[1]", *The Journal of Pharmacology and Experimental Therapeutics*, vol. 295, No. 3, pp. 1183–1191 (2000).
L. Guarneri et al., "The Effects of mCPP and Bladder voiding contractions in Rats are Mediated by the 5–HT$_{2A}$/5–HT$_{2c}$ Receptors", *Neurourol.Urodyn*, vol. 15, pp. 316–317 (1996).

(List continued on next page.)

Primary Examiner—Richard L. Raymond
(74) Attorney, Agent, or Firm—Fish & Richardson P.C.

(57) ABSTRACT

The invention relates to compounds of the general formula (I)

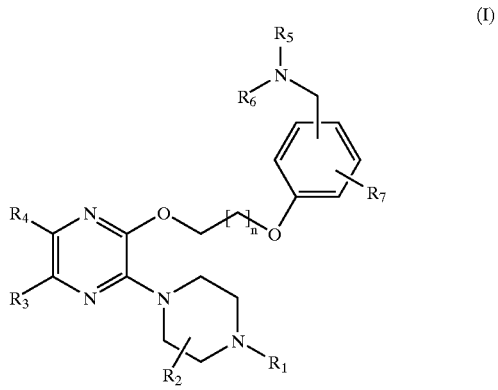

wherein R1, R2 and R3 are as described in the specification, which compounds are ligands to the serotonin 5-HT$_{2c}$ receptor.

22 Claims, No Drawings

OTHER PUBLICATIONS

John A. Harvey, "Serotonergic regulation of associative learning", *Behavioural Brain Research*, vol. 73, pp. 47–50 (1996).

Thomas F. Murray et al., "A comparison of the Analgesic Activities of 4,5,6,7–Tetrahydroisoxazolo[5,4–c] Pyridin–3–ol (Thip) and 6–Chloro–2[1–Piperazinyl] Pyrazine (MK 212)", *European Journal of Pharmacology*, vol. 90, pp. 179–184 (1983).

Roger M. Nitsch et al., "Serotonin 5–HT2a and 5–HT2c Receptors Stimulate Amyloid Precursor Protein Ectodormain Secretion", *The Journal of Biological Chemistry*, vol. 271, No. 8, pp. 4188–4194 (1996).

M.J. Piesla et al., "Atypical Antipsychotic–Like Effects of 5–HT2C Agonists", *Schizophrenia Research*, 49 (1–2), 95. Sp. Iss. SI Suppl. S Apr. 15, 2001.

Beatriz A. Rocha et al., "Enhanced Locomotor, Reinforcing, and Neurochemical Effects of Cocaine in Serotonin 5–Hydroxytryptamine 2C Receptor Mutant Mice", *The Journal of Neuoscience*, vol. 22, No. 22, pp. 10039–10045 (Nov. 15, 2002).

Richard B. Silverman, "Chapter 8, prodrugs and Drug Delivery Systems", *The Organic Chemistry of Drug Design and Drug Action*, pp. 352–361 (1992).

Robert E. Solomon et al., "Mechanisms of Effects of Intrathecal Serotonin on Nociception and Blood Pressure in Rats[1]", *The Journal of Pharmacology and Experimental Therapeutics*, vol. 245, No. 3, pp. 905–912 (1988).

William D. Steers et al., "Effects of m–chlorophenylpiperazine on penile and bladder functions in rats", *Am. J. Physiol.*, vol. 257, pp. R1441–R1449, (1989).

William D. Steers et al., "Effects of Serotonergic Agonists on Micturition and Sexual Function in the Rat", *Drug Development Research*, vol. 27, pp. 361–375 (1992).

Denise M. Tomkins et al., "An investigation of the role of $5-HT_{2c}$ receptors in modifying ethanol self–administration behaviour", *Pharmacology, Biochemistry and Behavior*, vol. 71, pp. 735–744 (2002).

Lee et al. *Effect of the Serotonin Agonist, MK–212, on Body Temperature in Schizophrenia.* Biological Psychiatry, 1992:31, pp. 460–470.

Lumma, Jr. et al. *Piperazinylpyrazines with Central Serolonimmimetric Activity.* Journal of Medicinal Chemistry, 1978, vol. 21, No. 6. pp. 536–542.

Jemrick–Luecke et al. *Involvement of $5-HT_{2A}$ receptors in the elevation of rat serum corticosterone concentrations by quipazine and MK–212.* European Journal of Pharmacology, vol. 311, 1996. pp. 217–211.

Conn et al. *Relative Efficacies of Piperazines at the Phosphoinositide Hydrolysis–Linked Serotonergic (5–HT–2 and 5–HT–1c) Receptors.* The Journal of Pharmacology and Experimental Therapeutics, vol. 242, No. 2, 1987. pp. 552–557.

* cited by examiner

COMPOUNDS AND THEIR USE

CROSS REFERENCE TO RELATED APPLICATIONS

This application claims priority from Swedish Patent Application No. 0004244-0, filed Nov. 20, 2000, and U.S. Provisional Patent Application Serial No. 60/253,702, filed Nov. 28, 2000. These applications are incorporated herein by reference in their entirety.

FIELD OF THE INVENTION

The present invention relates to novel compounds, to pharmaceutical compositions comprising the compounds, to processes for their preparation, as well as to the use of the compounds for the preparation of a medicament which particularly acts on the central nervous system.

BACKGROUND OF THE INVENTION

Many diseases of the central nervous system are influenced by the adrenergic, the dopaminergic, and the serotonergic neurotransmitter systems. For example, serotonin has been implicated in a number of diseases and conditions which originate in the central nervous system. A number of pharmacological and genetic experiments involving receptors for serotonin strongly implicate the 5-HT$_{2c}$ receptor subtype in the regulation of food intake (Obes. Res. 1995, 3, Suppl. 4, 449S–462S). The 5-HT$_{2c}$ receptor subtype is transcribed and expressed in hypothalamic structures associated with appetite regulation. It has been demonstrated that the 5-HT$_{2c}$ receptor agonist m-chlorophenylpiperazine (mCPP), which has some preference for the 5-HT$_{2c}$ receptor, reduces food intake in mice that express the normal 5-HT$_{2c}$ receptor while the compound lacks activity in mice expressing the mutated inactive form of the 5-HT$_{2c}$ receptor (Nature 1995, 374, 542–546). In a recent clinical study, a slight but sustained reduction in body weight was obtained after 2 weeks of treatment with mCPP in obese subjects (Psychopharmacology 1997, 133, 309–312). Recently, a series of pyrrolo[3,2,1-ij]quinoline derivatives was identified to be 5-HT$_{2C}$ receptor agonists having selectivity over the 5-HT$_{2A}$ receptor (Isaac M., et al., Bioorg. Med. Chem. Lett. 2000, 10, 919–921). The compounds are said to offer a novel approach to the treatment of obesity and epilepsy.

Weight reduction has also been reported from clinical studies with other "serotonergic" agents (see, e.g., IDrugs 1998, 1, 456–470). For example, the 5-HT reuptake inhibitor fluoxetine and the 5-HT releasing agent/reuptake inhibitor dexfenflurarnine have exhibited weight reduction in controlled studies. However, currently available drugs that increase serotonergic transmission appear to have only a moderate and, in some cases, transient effects on the body weight.

The 5-HT$_{2c}$ receptor subtype has also been suggested to be involved in CNS disorders such as depression and anxiety (Exp. Opin. Invest. Drugs 1998, 7, 1587–1599; IDrugs 1999, 2, 109–120).

The 5-HT$_{2c}$ receptor subtype has further been suggested to be involved in urinary disorders such as urinary incontinence (IDrugs 1999, 2, 109–120).

Compounds which have a selective effect on the 5-HT$_{2c}$ receptor may therefore have a therapeutic potential in the treatment of disorders like those mentioned above. Of course, selectivity also reduces the potential for adverse effects mediated by other serotonin receptors.

INFORMATION DISCLOSURE

U.S. Pat. No. 3,253,989 discloses the use of mCPP as an anorectic agent.

EP-A1-863 136 discloses azetidine and pyrrolidine derivatives which are selective 5-HT$_{2c}$ receptor agonists having antidepressant activity and which can be used for treating or preventing serotonin-related diseases, including eating disorders and anxiety.

EP-A-657 426 discloses tricyclic pyrrole derivatives having activity on the 5-HT$_{2c}$ receptor and which inter alia may be used for treating eating disorders.

EP-A-655 440 discloses 1-aminoethylindoles having activity on the 5-HT$_{2c}$ receptor and which may be used for treating eating disorders.

EP-A-572 863 discloses pyrazinoindoles having activity on the 5-HT$_{2c}$ receptor and which may be used for treating eating disorders.

J. Med. Chem. 1978, 21, 536–542 and U.S. Pat. No. 4,081,542 disclose a series of piperazinylpyrazines having central serotonin-mimetic activity.

J. Med. Chem. 1981. 24, 93–101 discloses a series of piperazinylquinoxalines with central serotoninmimetic activity.

WO 00/12475 discloses indoline derivatives as 5-HT$_{2b}$ and/or 5-HT$_{2C}$ receptor ligands, especially for the treatment of obesity.

WO 00/12510 discloses pyrroloindoles, pyridoindoles and azepinoindoles as 5-HT$_{2c}$ receptor agonists, particluarly for the treatment of obesity.

WO 00/12482 discloses indazole derivatives as selective, directly active 5-HT$_{2c}$ receptor ligands, preferably 5-HT$_{2c}$ receptor agonists, particularly for use as anti-obesity agents.

WO 00/12502 discloses pyrroloquinolines as 5-HT$_{2c}$ receptor agonists, particularly for use as anti-obesity agents.

WO 00/35922 discloses 2,3,4,4a-tetrahydro-1H-pyrazino [1,2-a]quinoxalin-5(6H)ones as 5HT$_{2c}$ agonists, which may be used for the treatment of obesity.

WO 00/44737 discloses aminoalkylbenzofurans as 5-HT$_{2c}$ agonists, which may be used for the treatment of obesity.

Further compounds reported to be 5HT$_{2c}$ receptor agonists are, for example, indazolylpropylamines of the type described in WO 00/12481; indazoles of the type described in WO 00/17170; piperazinylpyrazines of the type described in WO 00/76984; heterocycle fused γ-carbolines of the type described in WO 00/77001, WO 00/77002 and WO 00/77010; benzofurylpiperazines of the type described in WO 01/09111 and WO 01/09123; benzofurans of the type described in WO 01/09122; benzothiophenes of the type described in 01/09126; aminoalkylindazoles of the type described in WO 98/30548; indoles of the type described in WO 01/12603; indolines of the type described in WO 01/12602; pyrazino(aza)indoles of the type described in WO 00/44753 and tricyclic pyrroles or pyrazoles of the type described in WO 98/56768.

GB-B-1,457,005 discloses 1-piperazinyl-2-[2-(phenyl) ethenyl]-quinoxaline derivatives which exhibit anti-inflammatory activity.

Chem. Pharm. Bull. 1993, 41(10) 1832–1841 discloses 5-HT$_3$ antagonists including 2-(4-methyl-1-piperazinyl)-4-phenoxyquinoxaline.

GB-B-1,440,722 discloses 2-(1'-piperazinyl)-quinoxaline compounds having pharmaceutical activity against depression.

WO 96/11920 discloses CNS-active pyridinylurea derivatives.

WO 95/01976 discloses indoline derivatives active as $5\text{-HT}_{2c}$ antagonists and of potential use in the treatment of CNS disorders.

WO 97/14689 discloses arylpiperazine cyclic amine derivatives, which are selective $5\text{-HT}_{1d}$ receptor antagonists.

WO 98/42692 discloses piperazines derived from cyclic amines, which are selective antagonists of human $5\text{-HT}_{1a}$, $5\text{-HT}_{1d}$ and $5\text{-HT}_{1b}$ receptors.

GB-B-1,465,946 discloses substituted pyridazinyl, pyrimidinyl and pyridyl compounds which are active as β-receptor blocking agents.

EP-A-711757 discloses [3-(4-phenyl-piperazin-1-yl) propylamino]-pyridine, pyrimidine and benzene derivatives as α-adrenoceptor antagonists.

WO 99/03833 discloses arylpiperazine derivatives, which are $5\text{-HT}_2$ antagonists and $5\text{-HT}_{1a}$ receptor agonists and therefore are useful as remedies or preventives for psychoneurosis.

WO 96/02525 discloses arylpiperazine-derived piperazide derivatives having 5-HT receptor antagonistic activity.

WO 99/58490 disloses aryl-hydronaphthalen-alkane amines which may effectuate partial or complete blockage of serotonergic $5\text{-HT}_{2c}$ receptors in an organism.

OBJECT OF THE INVENTION

It is an object of the present invention to provide new compounds.

Another object of the invention is a pharmaceutical composition comprising compounds for use in therapy as an active ingredient.

Finally, an object of the invention is a method of treatment or prophylaxis of a serotonin related disease, especially a disease related to the $5\text{-HT}_{2c}$ receptor.

SUMMARY OF THE INVENTION

According to the invention novel compounds of the general formula (I) are provided:

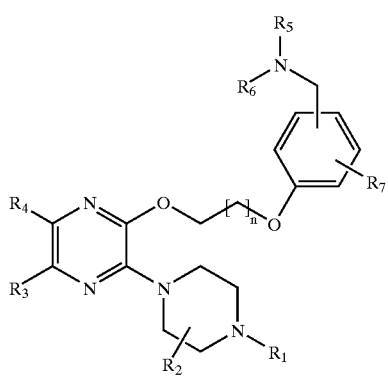

(I)

wherein
$R_1$ is hydrogen, $C_1$–$C_4$-alkyl, $C_{3\text{-}4}$-alkenyl, $C_{1\text{-}4}$-acyl, $C_{1\text{-}4}$-alkoxycarbonyl, 2-hydroxyethyl, 2-cyanoethyl, tetrahydropyran-2-yl, or a nitrogen protecting group;
$R_2$ is hydrogen, $C_{1\text{-}4}$-alkyl, hydoxymethyl, $C_{1\text{-}4}$-alkoxymethyl, or fluoromethyl;

$R_3$ and $R_4$ independently of each other are hydrogen, halogen, methyl, $C_{1\text{-}4}$-alkyl, aryl, heteroaryl wherein aryl and heteroaryl residues in turn may be substituted in one or more positions independently of each other by halogen, $C_{1\text{-}4}$-alkyl, $C_{1\text{-}4}$-alkoxy, $C_{1\text{-}4}$-alkylthio, $C_{1\text{-}4}$-alkylsulphonyl, methanesulphonamido, acetyl, nitro, cyano, hydroxy, trifluoromethyl, trifluoromethoxy, trifluoromethylthio, amino, methylamino, dimethylamino, or acetamido; or $R_3$ and $R_4$ together with the carbon atoms to which they are bound form a 5- or 6-membered aromatic or heteroaromatic ring, which optionally is independently substituted in one or more positions by halogen, methyl, methoxy, methylthio, methylsulphonyl, nitro, cyano, hydroxy, trifluoromethyl, trifluoromethylthio, amino, methylamino, dimethylamino or acetamido;

$R_5$ and $R_6$ independently of each other are hydrogen, $C_1$–$C_4$-alkoxy-$C_2$–$C_4$-alkyl, hydroxy-$C_2$–$C_4$-alkyl, $C_1$–$C_6$-alkyl, $C_2$–$C_6$-acyl, aryl, heteroaryl, aryl-$C_1$–$C_2$-alkyl, heteroaryl-$C_1$–$C_2$-alkyl, aryl-$C_1$–$C_2$-acyl, heteroaryl-$C_1$–$C_2$-acyl, and wherein any aryl or heteroaryl, alone or as part of another group, may be independently substituted in one or more positions by $C_{1\text{-}4}$-alkyl, $C_{1\text{-}4}$-alkoxy, $C_{1\text{-}4}$-alkylthio, $C_{2\text{-}4}$-acyl, $C_{1\text{-}4}$-alkylsulphonyl, cyano, nitro, hydroxy, $C_{2\text{-}3}$-alkenyl, $C_{2\text{-}3}$-alkynyl, fluoromethyl, trifluoromethyl, trifluoromethoxy, halogen, dimethylamino, or methylamino; or $R_5$ and $R_6$ together with the nitrogen atom to which they are bound form a saturated heterocyclic ring having 4–7 ring members which ring may contain an additional heteroatom and which may be substituted by methyl, oxo or hydroxy;

$R_7$ is hydrogen or a substituent selected from halogen, methyl, methoxy, and ethoxy; and n=1–3;

and pharmaceutically acceptable salts, hydrates, geometrical isomers, tautomers, optical isomers, N-oxides and prodrug forms thereof.

In case the compounds of formula (I) can be in the form of optical isomers, the invention comprises the racemic mixture as well as the individual enantiomers as such.

In case the compounds of formula (I) contain groups which may exist in tautomeric forms, the invention comprises the tautomeric forms of the compounds as well as mixtures thereof.

In case the compounds of formula (I) can be in the form of geometrical isomers, the invention comprises the geometrical isomers as well as mixtures thereof.

In another aspect, this invention provides a method for preparing a compound of this invention. The method includes converting a compound of formula (II):

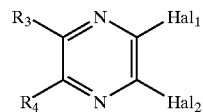

(II)

to the just-mentioned compound.

In formula (II), $R_3$ and $R_4$ independently of each other are hydrogen, halogen, methyl, $C_{1\text{-}4}$-alkyl, aryl, heteroaryl wherein aryl and heteroaryl residues in turn may be substituted in one or more positions independently of each other by halogen, $C_{1\text{-}4}$-alkyl, $C_{1\text{-}4}$-alkoxy, $C_{1\text{-}4}$-alkylthio, $C_{1\text{-}4}$-alkylsulphonyl, methanesulphonamido, acetyl, nitro, cyano, hydroxy, trifluoromethyl, trifluoromethoxy, trifluoromethylthio, amino, methylamino, dimethylamino or acetamido; or $R_3$ and $R_4$ together with the carbon atoms to which they are bound form a 5- or 6-membered aromatic or heteroaromatic ring, which may be substituted in one or more positions by halogen, methyl, methoxy, methylthio, methylsulphonyl, nitro, cyano, hydroxy, trifluoromethyl, trifluoromethylthio, amino, methylamino, dimethylamino or acetamido; and each of $Hal_1$ and $Hal_2$, independently, is halogen.

In further another aspect, the invention provides the compounds according to formula (I) above for use in therapy.

Still another aspect of the invention provides a pharmaceutical composition comprising a compound according to formula (I) above as the active ingredient, preferably together with a pharmaceutically acceptable carrier and, if desired, other pharmacologically active agents.

In yet another aspect, the invention provides a method for the treatment of a human or animal subject suffering from a serotonin-related disease, particularly 5-$HT_{2c}$ receptor-related, especially eating disorders, particularly obesity; memory disorders, schizophrenia, mood disorders, anxiety disorders, pain, substance abuse, sexual dysfunctions, epilepsy and urinary disorders.

Another aspect of the invention provides the use of the compounds according to formula (I) above for the manufacture of a medicament for the treatment of a serotonin-related disease, particularly 5-$HT_{2c}$ receptor-related, especially eating disorders, particularly obesity; memory disorders; schizophrenia, mood disorders, anxiety disorders, pain, substance abuse, sexual dysfunctions, epilepsy and urinary disorders.

Finally a method for modulating $5HT_{2c}$ receptor function is an aspect of the invention.

DETAILED DESCRIPTION OF THE INVENTION

According to the present invention, a class of novel compounds has been developed which bind to the 5-$HT_{2c}$ receptor (agonists or antagonists) and which therefore may be used for the treatment of serotonin-related disorders.

First, the various terms used, separately and in combinations, in the above definition of the compounds having the general formula (I) will be explained.

By "heteroatom" is meant nitrogen, oxygen, sulphur, and in heteroaromatic rings, also selenium.

The term "aryl" includes phenyl, 1-naphthyl and 2-naphthyl.

The term "heteroaryl" includes five- and six-membered heteroaromatic rings such as pyrrole, imidazole, thiophene, furan, selenophene, thiazole, isothiazole, thiadiazole, oxazole, isoxazole, oxadiazole, pyridine, pyrazine, pyrimidine, pyridazine, pyrazole, triazole and tetrazole.

$C_{1-6}$-alkyl, which may be straight or branched, is preferably $C_{1-4}$-alkyl. Exemplary alkyl groups include methyl, ethyl, propyl, isopropyl, butyl, sec-butyl, tert-butyl, pentyl, isopentyl, hexyl, and isohexyl.

$C_{1-4}$-alkoxy may be straight or branched. Exemplary alkoxy groups include methoxy, ethoxy, propoxy, isopropoxy, butoxy, sec-butoxy and tert-butoxy.

$C_{2-4}$-alkenyl may be straight or branched. Exemplary alkenyl groups include vinyl, 2-propenyl and 1-methyl-2-propenyl.

$C_1$–$C_4$-alkoxy-$C_2$–$C_4$-alkyl may be straight or branched. Exemplary groups include 2-(methoxy)ethyl, 3-methoxy-1-propyl, 4-ethoxy-1-butyl and the like.

Exemplary aryl-$C_1$–$C_2$-acyl include benzoyl and phenylacetyl. Exemplary heteroaryl-$C_1$–$C_2$-acyl include nicotinoyl and 3-pyridinylacetyl and the like.

$C_{2-4}$-acyl may be saturated or unsaturated. Exemplary acyl groups include acetyl, propionyl, butyryl, isobutyryl, and butenoyl (e.g. 3-butenoyl).

Halogen includes fluorine, chlorine and bromine.

Where it is stated above that aryl and heteroaryl residues may be substituted, this applies to aryl and heteroaryl per se as well as to any combined groups containing aryl or heteroaryl residues, such as heteroaryl-$C_1$–$C_2$-alkyl and aryl-$C_1$–$C_2$-acyl.

The term "N-oxides" means that one or more nitrogen atoms, when present in a compound, are in N-oxide form (N→O).

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, $8^{th}$ ed., McGraw-Hill, Int. Ed. 1992, "Biotransformation of Drugs, p. 13–15.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, toluenesulphonic acid, methanesulphonic acid, fumaric acid, succinic acid, tartaric acid, citric acid, benzoic acid, ascorbic acid, and the like.

$R_1$ is preferably hydrogen or methyl. Most preferably $R_1$ is hydrogen.

$R_1$ may also serve as a nitrogen protecting group, and then $R_1$ is t-butoxycarbonyl (t-BOC), benzyl, or trityl.

$R_2$ is preferably hydrogen or methyl (especially in the 2-position of the piperazine ring).

$R_3$ and $R_4$ are preferably (independently) hydrogen, halogen or methyl. When $R_3$ and $R_4$ form a ring together with the ring carbons to which they are bound, such a ring is preferably benzene (to give quinoxaline) or thiophene (to give thieno[3,4-b]pyrazine). When substituted, the rings are preferably mono- or disubstituted, preferably by halogen or methyl.

When $R_7$ is other than hydrogen it may occupy any available position of the phenyl ring.

The group —$CH_2N(R_5)(R_6)$ may be attached to the orto-, meta-, or the para position, relative to the alkylenedioxy side-chain, of the phenyl ring, preferably the meta position.

n in formula (I) is 1–3 where n is the number of methylene groups n is preferably 1, having the meaning that the two oxygen atoms in formula (I) are spaced between a —$CH_2CH_2$— group;

Preferred compounds of the general formula (I) above are:

2-(1-Piperazinyl)-3-{2-[3-(4-morpholinylmethyl)phenoxy]ethoxy}pyrazine;

2-(1-Piperazinyl)-3-{2-[3-(1-pyrrolidinylmethyl)phenoxy]ethoxy}pyrazine;

2-(1-Piperazinyl)-3-{2-[3-(4-methyl-1-piperazinylmethyl)phenoxy]ethoxy}pyrazine;

2-(1-Piperazinyl)-3-{2-[3-{(2-methoxyethyl)amino}methyl)phenoxy]ethoxy}pyrazine;

2-(1-Piperazinyl)-3-{2-[3-{(isopropylamino)methyl}phenoxy]ethoxy}pyrazine, and their pharmacologically acceptable salts and solvates.

In another aspect, this invention relates to compounds of any of the formulae herein and their use as delineated herein, wherein $R_5$ and $R_6$ together with the nitrogen atom to which they are bound form a saturated heterocylic ring having 4–7 ring members, and which may contain an additional heteratom. Exemplary rings are azetidine, pyrrolidine, piperazine, homopiperazine, morpholine, thiomorpholine, or piperidine. The saturated heterocyclic ring may be substituted by methyl, oxo, or hydroxy.

As mentioned above, the compounds of the present invention are useful for the treatment (including prophylactic treatment) of serotonin-related disorders, especially 5-$HT_{2c}$ receptor-related, in a human being or in an animal (including e.g. pets), such as eating disorders, especially obesity; memory disorders, such as Alzheimer's disease; schizophrenia; mood disorders, including, but not restricted to, major depression and bipolar depression, including both mild and manic bipolar disorder, seasonal affective disorder (SAD); anxiety disorders, including situational anxiety, generalised anxiety disorder, primary anxiety disorders (panic disorders, phobias, obsessive-compulsive disorders, and post-traumatic stress disorders), and secondary anxiety disorders (for example anxiety associated with substance abuse); pain; substance abuse; sexual dysfunctions; epilepsy and urinary disorders, such as urinary incontinence.

The compounds of the present invention in radiolabeled form, may be used as a diagnostic agent.

The compounds of the general formula (I) above may be prepared by a method of this invention, or by, in analogy with, a conventional method. This invention relates to methods of making compounds of any formulae herein comprising reacting any one or more of the compounds or formulae delineated herein including any processes delineated herein.

For example, as shown in Scheme 1, a compound of formula (I) may be prepared by first treating a compound of formula (II), wherein Hal is halogen and $R_3$ and $R_4$ are as defined above, with an appropriate piperazine of formula (III), wherein $R_1$ and $R_2$ have the same meaning as in formula (I) and where $R_1$ may be a suitable nitrogen protecting group, such as trityl, benzyl or tert-butoxycarbonyl, to provide a compound of formula (IV). The reaction is carried out in a solvent, such as, acetonitrile, dioxane, tetrahydrofuran (THF), n-butanol, N,N-dimethylformamide (DMF), or in a mixture of solvents such as DMF/dioxane, optionally in the presence of a base, such as $K_2CO_3$, $Na_2CO_3$, $Cs_2CO_3$, NaOH, triethylamine, pyridine, or the like, at 0–200° C. for 1–24 hours.

The compound of formula (IV) is reacted with a diol of formula (V), wherein n has the same meaning as in formula (I), to provide intermediate (VI). The reaction is carried out in a solvent, such as, dioxane, THF, DMF or pyridine, and the like, in the presence of a base such as K-t-BuO, Na-t-BuO, NaH, or the like, at 0–150° C. for 1–24 hours.

Intermediate (VI) is reacted with a hydroxybenzaldehyde compound of formula (VII), wherein $R_7$ has the same meaning as in formula (I), to provide the aldehyde intermediate (VIII). The reaction may be carried out in the presence of diethyl azodicarboxylate (DEAD) or 1,1'-azobis(N,N-dimethylformamide) (cf. Tetrahedron Lett. 1995, 36, 3789–3792), preferably DEAD, and triphenylphosphine ($PPh_3$) in a solvent such as THF or dichloromethane (Mitsunobu reaction; see: Org. React. 1992, 42, 335–656.).

Subjecting intermediate (VIII) to a standard reductive alkylation procedure (such as described in J. Org. Chem. 1996, 61, 3849–3862), with an appropriate amine of formula (IX), wherein $R_5$ and $R_6$ have the same meaning as in formula (I), results in a compound of this invention (I).

When $R_1$ in formula (I) is a nitrogen protecting group as defined below, the subsequent N-deprotection may be performed under standard conditions, such as those described in Protective Groups in Organic Synthesis, John Wiley & Sons, 1991, to provide compounds of formula (I) wherein $R_1$ is hydrogen. Nitrogen protecting groups are known in the art and include those described in T. W. Greene and P. G. M. Wuts, Protective Groups in Organic Synthesis, 2d. Ed., John Wiley and Sons (1991) and subsequent editions thereof.

Scheme 1.

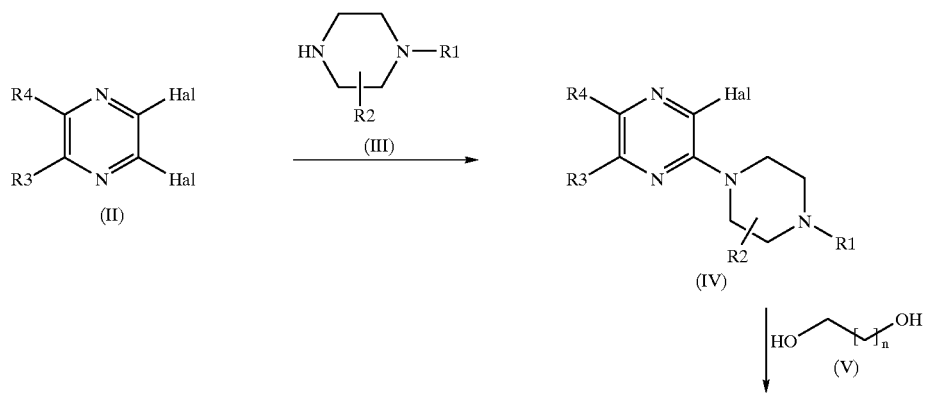

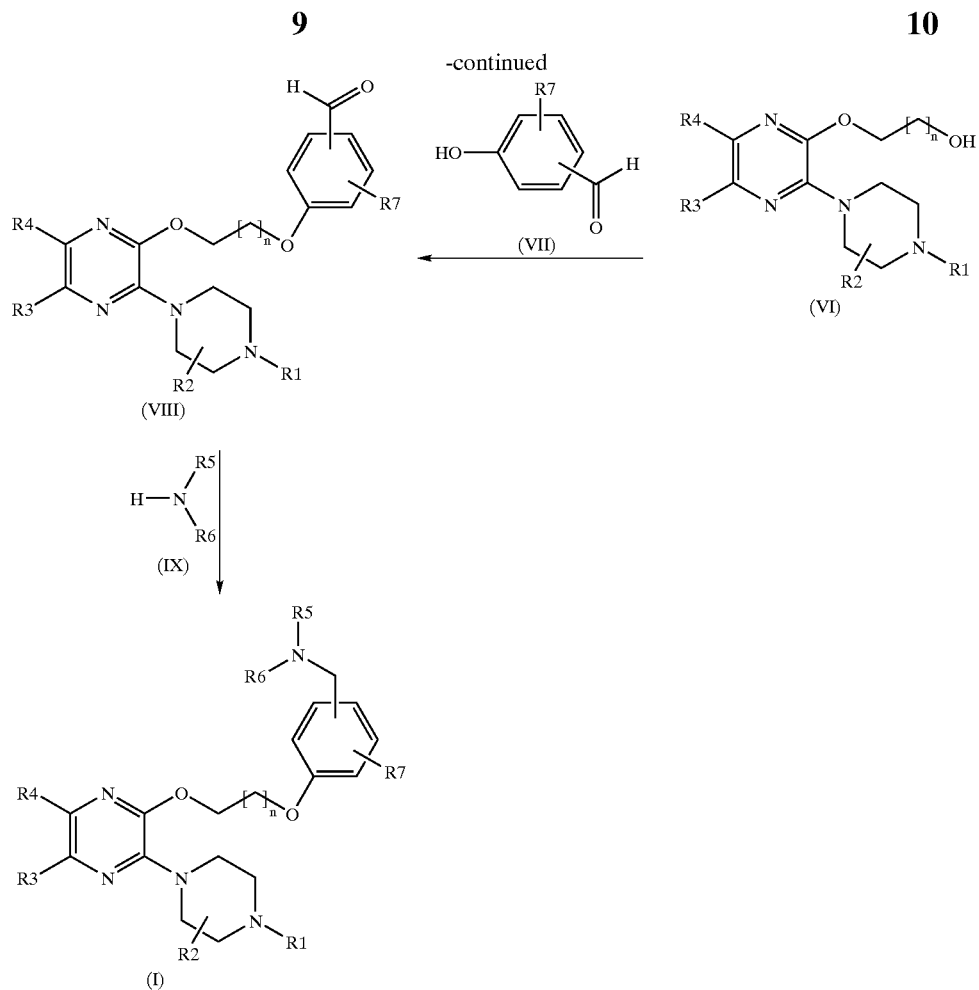

An obtained compound of formula (I) may be converted to another compound of formula (I) by methods well known in the art.

The processes described above may be carried out to give a compound of the invention in the form of a free base or as an acid addition salt. A pharmaceutically acceptable acid addition salt may be obtained by dissolving the free base in a suitable organic solvent, such as ether or in a mixture of ether and methanol, and treating the solution with an acid, in accordance with conventional procedures for preparing acid addition salts from base compounds. Examples of addition salt forming acids are maleic acid, fumaric acid, succinic acid, methanesulfonic acid, acetic acid, oxalic acid, benzoic acid, hydrochloric acid, sulphuric acid, phosphoric acid, and the like.

The compounds of formula (I) may possess one or more chiral carbon atoms, and they may therefore be obtained in the form of optical isomers, e.g., as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

In accordance with the present invention, the compounds of formula (I), in the form of free bases or salts with physiologically acceptable acids, can be brought into suitable galenic forms, such as compositions for oral use, for injection, for nasal spray administration or the like, in accordance with accepted pharmaceutical procedures. Such pharmaceutical compositions according to the invention comprise an effective amount of the compounds of formula (I) in association with compatible pharmaceutically acceptable carrier materials, or diluents, as are well known in the art. The carriers may be any inert material, organic or inorganic, suitable for enteral, percutaneous, subcutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavouring agents, buffers, and the like.

The compositions according to the invention can e.g. be made up in solid or liquid form for oral administration, such as tablets, pills, capsules, powders, syrups, elixirs, dispersable granules, cachets, suppositories and the like, in the form of sterile solutions, suspensions or emulsions for parenteral administration, sprays, e.g. a nasal spray, transdermal preparations, e.g. patches, and the like.

As mentioned above, the compounds of the invention may be used for the treatment of serotonin-related disorders in a human being or an animal, such as eating disorders, particularly obesity, memory disorders, schizophrenia, mood disorders, anxiety disorders, pain, substance abuse, sexual dysfunctions, epilepsy and urinary disorders. The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

General

NMR spectra were recorded on a Bruker Advance DPX 400 MHz spectrometer at 25° C. Chemical shifts are given in ppm relative to tetramethylsilane. LC/MS data were obtained using an HP1100 hplc system coupled to a Micromass platform LC mass spectrometer running MassLynx. Details of the hplc are: Column, Phenomenex C18 Luna, 30×46 mm at 40±1° C. Eluant gradient T=0, 95% (0.1% formic acid in water) and 5% (0.1% formic acid in acetonitrile, then a linear gradient to T=2.5 min, 5% (0.1% formic acid in water) and 95% (0.1% formic acid in acetonitrile), then a further 1 min at these conditions. Eluent flow rate was 2 mL/min. Detection was by UV diode array at window 210–400 nm. Alternate +ve and −ve ion APCI mass spectra were collected throughout the 3.5 min, scanning between 100 and 650 mass units. High resolution MS were obtained on a Micromass LCT spectrometer. Developing solvents for TLC on silica were di-isopropylether or ethyl acetate/light petroleum mixtures.

Example 1

2-(1-Piperazinyl)-3-{2-[3-(4-morpholinylmethyl) phenoxy]ethoxy}pyrazine

Step 1: 2-Chloro-3-(4-tert-butoxycarbonyl-1-piperazinyl) pyrazine. The title compound was prepared according to the procedure described in WO 00/76984. A mixture of N-Boc-piperazine (11.47 g, 61.5 mmol), $K_2CO_3$ (8.5 g, 61 mmol) and 2,3-dichloropyrazine (9.20 g, 61.7 mmol) in acetonitrile (100 mL) was stirred at 100° C. for 40 h. The reaction mixture was concentrated, dissolved in toluene, washed with water, dried ($MgSO_4$), and concentrated. The residue was purified by chromatography on silica gel using toluene/EtOAc (7:3) as eluent to give 18.3 g (100%) of the title product. HRMS m/z calcd for $C_{13}H_{19}N_4O_2$ (M)$^+$298.1197, found 298.1206.

Step 2: 2-[3-(4-tert-Butoxycarbonyl-1-piperazinyl)-2-pyrazinyloxy]ethanol. The title compound was prepared according to the procedure described in WO 00/76984. KO-t-Bu (9.92 g, 103 mmol) was added to a mixture of the product obtained in step 1 (18.14 g, 60.7 mmol) and ethylene glycol (25 mL, 448 mmol) in pyridine (125 mL) at 85° C. The reaction mixture was stirred for 15 h and then poured into ice-water and extracted with toluene. The organic phase was dried ($MgSO_4$) and concentrated. The residue was purified by chromatography on silica gel using toluene/EtOAc (1:1) as eluent to give 16.9 g (85%) of the title product. HRMS m/z calcd for $C_{15}H_{24}N_4O_4$ (M)$^+$ 324.1798, found 324.1784.

Step 3: tert-Butyl 4-{3-[2-(3-formylphenoxy)ethoxy]-2-pyrazinyl}-1-piperazinecarboxylate.

A solution of the compound obtained in step 2 above (1.5 g, 4.7 mmol) in dry tetrahydrofuran (THF; 10 mL) was treated with 3-hydroxybenzaldehyde (0.74 g, 6.06 mmol) and triphenylphosphine (1.59 g, 6.06 mmol). This solution was stirred at room temperature then treated with diethyl azodicarboxylate (0.96 mL, 6.06 mmol) in dry THF (5 mL). After 1 hr, TLC indicated some remaining 2-[3-(4-tert-butoxycarbonyl-1-piperazinyl)-2-pyrazinyloxy]ethanol. The reaction was heated at reflux under nitrogen for 5 h, then left to cool to room temperature overnight. TLC again showed unreacted starter. The mixture was treated with further triphenylphosphine (0.80 g, 3.03 mmol), diethyl azodicarboxylate (0.5 mL, 3.03 mmol) and 3-hydroxybenzaldehyde (0.40 g, 3.03 mmol), then stirred at RT for a further 3 hrs (reaction complete by TLC). The volatiles were removed in vacuo and the residue was purified by flash column on silica gel, eluting with petroleum ether/ethyl acetate (2:1). This furnished 0.33 g (16%) of the title product as a colourless oil. $^1$H NMR (CDCl$_3$) δ 1.5 (s, 9H); 3.5 (bs, 8H), 4.45 (m, 2H); 4.75 (m, 2H); 7.2 (d, 1H); 7.45 (s, 1H); 7.5 (m, 2H); 7.6 (s, 1H); 7.75 (s, 1H).

Step 4: tert-Butyl 4-(3-{2-[3-(4-morpholinylmethyl) phenoxy]ethoxy}-2-pyrazinyl)-1-piperazinecarboxylate.

A stirred solution of the aldehyde from step 3 above (71.2 mg, 0.166 mmol) in 1,2-dichloroethane (5 mL) was treated with morpholine (19 mg, 0.22 mmol), 3 Å molecular sieves and sodium triacetoxyborohydride (52 mg, 0.25 mmol). The mixture was stirred at room temperature for 5 h (TLC monitoring). The solution was filtered and the filtrate was treated with an excess of saturated aqueous sodium bicarbonate. The ether extracts were separated and dried over magnesium sulfate. The mixture was filtered and solvent was removed in vacuo to give 54 mg (65%) of the title product as a yellow oil. Pure by NMR. $^1$H NMR (CDCl$_3$) δ 1.4 (s, 9H); 2.35 (m, 4H); 3.4 (m, 10H); 3.65 (m, 4H); 4.3 (m, 2H); 4.65 (m, 2H); 6.75 (d, 1H); 6.9 (m, 2H); 7.2 (t, 1H); 7.5 (s, 1H); 7.7 (s, 1H).

Step 5: 2-(1-Piperazinyl)-3-{2-[3-(4-morpholinylmethyl) phenoxy]ethoxy}pyrazine.

The product from step 4 above (54 mg, 0.1 1 mmol) was dissolved in dry ether (20 mL), stirred at room temperature and treated with hydrogen chloride in ether (~6 M; 5 mL). The resulting white suspension was stirred for 2 h, then quickly filtered off. The hydrochloride salt (hygroscopic), was dissolved in water and neutralized with sodium carbonate. The free base was extracted into dichloromethane. The organic layers were dried magnesium sulfat, filtered, and concentrated in vacuo to furnish 13 mg (29%) of the title product as a pale yellow oil. LS/MS purity 100%. $^1$H NMR (CDCl$_3$) δ 1.8 (b, 1H); 2.45 (m, 4H); 2.95 (m, 4H); 3.45 (s, 2H); 3.55 (m, 4H); 3.7 (m, 4H); 4.35 (t, 2H); 4.7 (t, 2H); 6.85 (d, 1H); 6.95 (m, 2H); 7.25 (t, 1H); 7.55 (s, 1H); 7.75 (s, 1H).

The following compounds were prepared analogously from tert-butyl 4-{3-[2-(3-formylphenoxy)ethoxy]-2-pyrazinyl}-1-piperazinecarboxylate (obtained in Example 1, Step 3) and the requisite amine.

Example 2

2(1-Piperazinyl)-3-{2-[3-(1-pyrrolidinylmethyl) phenoxy]ethoxy}pyrazine

Yield 31%. LS/MS purity 100%. $^1$H NMR (CDCl$_3$) δ 1.7 (m, 4H); 2.45 (m, 4H); 2.9 (m, 4H); 3.4 (m, 4H); 3.5 (s, 2H);

4.3 (m, 2H); 4.6 (m, 2H); 6.7 (d, 1H); 6.85 (m, 2H); 7.15 (t, 1H); 7.45 (s, 1H); 7.7 (s, 1H).

Example 3

2(1-Piperazinyl)-3-{2-[3-(4-methyl-1-piperazinylmethyl)phenoxy]ethoxy}pyrazine

Yield 56%. LS/MS purity 100%. $^1$H NMR (CDCl$_3$) δ 2.15 (s, 3H); 2.35 (b, 9H); 2.85 (m, 4H); 3.35 (m, 6H); 4.2 (m, 2H); 4.55 (m, 2H); 6.7 (d, 1H); 6.8 (m, 2H); 7.1 (t, 1H); 7.4 (s, 1H); 7.6 (s, 1H).

Example 4

2(1-Piperazinyl)-3-{2-[3-{(2-methoxyethyl)amino}methyl)phenoxy]ethoxy}pyrazine

Yield 37%. LS/MS purity 100%. $^1$H NMR (CDCl$_3$) δ 2.8 (t, 2H); 3.05 (m, 6H); 3.35 (s, 3H); 3.6 (m, 6H); 3.8 (s, 2H); 4.35 (m, 2H); 4.7 (m, 2H); 6.8 (d, 1H); 6.95 (d, 2H); 7.25 (t, 1H); 7.55 (s, 1H); 7.8 (s, 1H).

Example 5

2-(1-Piperazinyl)-3-{2-[3-{(isopropylamino)methyl}phenoxy]ethoxy}pyrazine

Yield 60%. LS/MS purity 100%. $^1$H NMR(CDCl$_3$) δ 1.1 (d, 6H); 1.85 (b, 1H); 2.85 (m, 1H); 3.0 (m, 4H); 3.5 (m, 4H); 3.8 (s, 2H); 4.35 (m, 2H); 4.7 (m, 2H); 6.8 (d, 1H); 6.9 (m, 2H); 7.2 (t, 1H); 7.5 (s, 1H); 7.75 (s, 1H).

Example 6

2-(1-Piperazinyl)-3-{2-[3-{(3-methoxyphenylamino)methyl}phenoxy]ethoxy}pyrazine

LC/MS purity 100%.

Example 7

2-(1-Piperazinyl)-3-{2-[3-{(2-hydroxyethylamino)methyl}phenoxy]ethoxy}pyrazine

LC/MS purity 97%.

Preparation of Pharmaceutical Compositions

| | EXAMPLE: preparation of tablets | |
|---|---|---|
| | Ingredients | mg/tablet |
| 1. | Active compound | 10.0 |
| 2. | Cellulose, microcrystalline | 57.0 |
| 3. | Calcium hydrogen phosphate | 15.0 |
| 4. | Sodium starch glycolate | 5.0 |
| 5. | Silicon dioxide, colloidal | 0.25 |
| 6. | Magnesium stearate | 0.75 |

The active ingredient 1 is mixed with ingredients 2, 3, 4 and 5 for about 10 minutes. The magnesium stearate is then added, and the resultant mixture is mixed for about 5 minutes and compressed into tablet form with or without film-coating.

Pharmacological Tests

The ability of a compound of the invention to bind or act at specific 5-HT receptor subtypes can be determined using in vitro and in vivo assays known in the art. The biological activity of compounds prepared in the Examples was tested using different tests.

Affinity Assay

The 5-HT$_{2c}$ receptor affinity of compounds in the Examples was determined in competition experiments, where the ability of each compound in serial dilution to displace $^3$H-labelled 5-HT, bound to membranes prepared from a transfected HEK293 cell line stably expressing the human 5-HT$_{2c}$ receptor protein, was monitored by Scintillation Proximity Assay technology. Non-specific binding was defined using 5 μM mianserin. Results obtained for exemplary compounds of the invention are illustrated in Table 1 below. Typically, the 5HT$_{2c}$ receptor affinity values (K$_i$, nM) were in the range of 1 nM to 1500 nM, preferably 1 nM to 100 nM.

TABLE 1

5-HT$_{2c}$ Receptor Affinity

| Compound | Ki (nM) |
|---|---|
| Example 1 | 18 |
| Example 5 | 3 |

Efficacy Assay

The agonist efficacy at the 5-HT$_{2c}$ receptor of the compounds in the Examples was determined by the ability of each compound to mobilise intracellular calcium in transfected HEK293 cells, stably expressing the human 5-HT$_{2c}$ receptor protein, using the calcium-chelating fluorescent dye FLUO-3 (Sigma, St. Louis, Mo., U.S.A.).

Typically, the maximum responses of 5-HT$_{2c}$ agonists were in the range of 15–100% relative to the maximum response of 5-HT (serotonin) at a concentration of 1 μM.

What is claimed is:

1. A compound of the general formula (I):

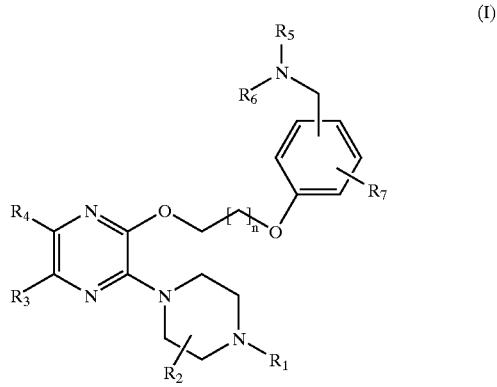

wherein

R$_1$ is hydrogen, C$_{1-4}$alkyl, C$_{3-4}$-alkenyl, C$_{1-4}$-acyl, C$_{1-4}$-alkoxycarbonyl, 2-hydroxyethyl, 2-cyanoethyl, tetrahydropyran-2-yl, or a nitrogen protecting group;

R$_2$ is hydrogen, C$_{1-4}$-alkyl, hydroxymethyl, C$_{1-4}$-alkoxymethyl, or fluoromethyl;

R$_3$ and R$_4$ independently of each other are hydrogen, halogen, methyl, C$_{1-4}$-alkyl, aryl, or heteroaryl wherein aryl and heteroaryl residues in turn may be substituted in one or more positions independently of each other by halogen, C$_{1-4}$-alkyl, C$_{1-4}$-alkoxy, C$_{1-4}$-alkylthio, C$_{1-4}$-alkylsulphonyl, methanesulphonamido, acetyl, nitro, cyano, hydroxy, trifluoromethyl, trifluoromethoxy, trifluoromethylthio, amino, methylamino, dimethylamino, or acetamido;

R$_5$ and R$_6$ independently of each other are hydrogen, C$_1$–C$_4$-alkoxy-C$_2$–C$_4$-alkyl, hydroxy-C$_2$–C$_4$-alkyl, $C_1-C_6$-alkyl, $C_2-C_6$-acyl, aryl, heteroaryl, aryl-$C_1-C_2$-alkyl, heteroaryl-$C_1-C_2$-alkyl, aryl-$C_1-C_2$-acyl, heteroaryl-$C_1-C_2$-acyl, and wherein any aryl or heteroaryl, alone or as part of another group, may be independently substituted in one or more positions by $C_{1-4}$-alkyl, $C_{1-4}$-alkoxy, $C_{1-4}$-alkylthio, $C_{2-4}$-acyl, $C_{1-4}$-alkylsulphonyl, cyano, nitro, hydroxy, $C_{2-3}$-alkenyl, $C_{2-3}$-alkynyl, fluoromethyl, trifluoromethyl, trifluoromethoxy, halogen, dimethylamino, or methylamino; or $R_5$ and $R_6$ together with the nitrogen atom to which they are bound form a saturated heterocyclic ring having 4–7 ring members which ring may contain an additional heteroatom and which may be substituted by methyl, oxo, or hydroxy;

$R_7$ is hydrogen or a substituent selected from halogen, methyl, methoxy, and ethoxy; and n=1–3;

and pharmaceutically acceptable salts, solvates, hydrates, geometrical isomers, tautomers, optical isomers, N-oxides or prodrug forms thereof.

2. The compound according to claim 1, wherein $R_1$ is hydrogen or methyl.

3. The compound according to claim 1, wherein $R_1$ is hydrogen.

4. The compound according to claim 1, wherein $R_2$ is hydrogen or methyl.

5. The compound according to claim 1, wherein $R_3$ and $R_4$ independently are hydrogen, halogen or methyl.

6. The compound according to claim 1, wherein $R_3$ and $R_4$ both are hydrogen.

7. The compound according to claim 1, wherein $R_7$ is hydrogen.

8. The compound according to claim 1, wherein $R_7$ is hydrogen and the group

—$CH_2N(R_5)(R_6)$ is attached to the meta-position, relative to the alkylenedioxy side-chain, of the phenyl ring.

9. The compound according to claim 1, wherein $R_5$ and $R_6$ together with the nitrogen atom to which they are bound form a ring selected from azetidine, pyrrolidine, piperazine, homopiperazine, morpholine, thiomorpholine, and piperidine.

10. The compound according to claim 1, wherein n=1.

11. The compound according to claim 1, selected from 2-(1-Piperazinyl)-3-{2-[3-(4-morpholinylmethyl)phenoxy]ethoxy}pyrazine;

2-(1-Piperazinyl)-3-{2-[3-(1-pyrrolidinylmethyl)phenoxy]ethoxy}pyrazine;

2-(1-Piperazinyl)-3-{2-[3-(4-methyl-1-piperazinylmethyl)phenoxy]ethoxy}pyrazine;

2-(1-Piperazinyl)-3-{2-[3-{(2-methoxyethyl)amino}methyl)phenoxy]ethoxy}pyrazine; and 2-(1-Piperazinyl)-3-{2-[3-{(isopropylamino)methyl}phenoxy]ethoxy}pyrazine and their pharmacologically acceptable salts and solvates.

12. A method for preparing a compound of claim 1, the method comprising contacting a compound of formula (II):

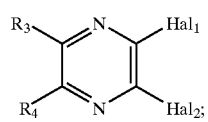

(II)

wherein $R_3$ and $R_4$ independently of each other are hydrogen, methyl, $C_{1-4}$-alkyl, aryl, heteroaryl wherein aryl and heteroaryl residues in turn may be substituted in one or more positions independently of each other by halogen, $C_{1-4}$-alkyl, $C_{1-4}$-alkoxy, $C_{1-4}$-alkylthio, $C_{1-4}$-alkylsulphonyl, methanesulphonamido, acetyl, nitro, cyano, hydroxy, trifluoromethyl, trifluoromethoxy, trifluoromethylthio, amino, methylamino, dimethylamino, or acetamido; and each of $Hal_1$ and $Hal_2$, independently, is halogen;

with a compound of formula (III):

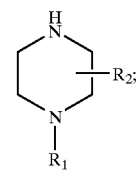

(III)

wherein $R_1$ is hydrogen or $C_{1-4}$ alkyl, $C_{3-4}$-alkenyl, $C_{1-4}$-acyl, $C_{1-4}$-alkoxycarbonyl, 2-hydroxyethyl, 2-cyanoethyl or tetrahydropyran-2-yl, or a nitrogen protecting group; and $R_2$ is hydrogen, $C_{1-4}$-alkyl, hydroxymethyl, $C_{1-4}$-alkoxymethyl or fluoromethyl;

to form a first intermediate (IV);

contacting the first intermediate (IV) with a compound of formula (V):

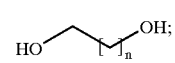

(V)

wherein n is 1–3;

to form a second intermediate (VI);

contacting the second intermediate (VI) with a compound of formula (VII):

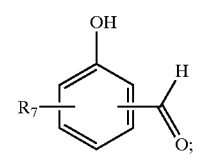

(VII)

wherein $R_7$ is hydrogen or a substituent selected from halogen, methyl, methoxy, and ethoxy, to form a third intermediate (VIII);

contacting the third intermediate (VIII) with a compound of formula (IX):

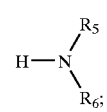

(IX)

wherein $R_5$ and $R_6$ independently of each other are hydrogen, $C_1-C_4$-alkoxy-$C_2-C_4$-alkyl, hydroxy-$C_2-C_4$-alkyl, $C_1-C_6$-alkyl, $C_2-C_6$-acyl, aryl, heteroaryl aryl-$C_1-C_2$-alkyl, heteroaryl-$C_1-C_2$-alkyl, aryl-$C_1-C_2$-acyl, or heteroaryl-$C_1-C_2$-acyl, and wherein any aryl or heteroaryl, alone or as part of another group, may be independently substituted in one or more positions by $C_{1-4}$-alkyl, $C_{1-4}$-alkoxy, $C_{1-4}$-alkylthio, $C_{2-4}$-acyl, $C_{1-4}$-alkylsulphonyl, cyano, nitro, hydroxy, $C_{2-3}$-alkenyl, $C_{2-3}$-alkynyl, fluoromethyl, trifluoromethyl, trifluoromethoxy, halogen, dimethylamino, or methylamino; or $R_5$ and $R_6$ together with the nitrogen atom to which they are bound form a saturated heterocyclic ring having 4–7 ring members which ring may contain an additional heteroatom and which may be substituted by methyl, oxo or hydroxy; to form the compound of claim 1.

13. The method according to claim 12, wherein $R_1$ is hydrogen or methyl.

14. The method according to claim 12, wherein $R_2$ is hydrogen or methyl.

15. The method according to claim 12, wherein $R_3$ and $R_4$ both are hydrogen.

16. The method according to claim 12, wherein $R_5$ and $R_6$ together with the nitrogen atom to which they are bound form a ring selected from azetidine, pyrrolidine, piperazine, homopiperazine, morpholine, thiomorpholine or piperidine.

17. A pharmaceutical composition comprising a compound according to claim 1 as an active ingredient, together with a pharmacologically and pharmaceutically acceptable carrier.

18. A method for the prophylaxis or treatment of a serotonin-related disease in a human being or in an animal, which method comprises administering to a subject in need thereof an effective amount of a compound according to claim 1.

19. The method according to claim 18 wherein said disease is a $5\text{-HT}_{2c}$ receptor-related disease.

20. The method according to claim 18 wherein said disease is selected from eating disorders, memory disorders, schizophrenia, mood disorders, anxiety disorders, pain, substance abuse, sexual dysfunctions, epilepsy and urinary disorders.

21. The method according to claim 20 wherein the eating disorder is obesity.

22. A method for modulating $5\text{HT}_{2c}$ receptor functions in a human being or animal, comprising administering to a subject in need thereof an effective amount of a compound according to claim 1.

* * * * *